(12) United States Patent
Chen et al.

(10) Patent No.: US 6,313,338 B1
(45) Date of Patent: Nov. 6, 2001

(54) PROCESS FOR PREPARING N-[1-(S)-ETHYOXYCARBONYL-3-PHENYLPROPYL]-L-ANANINE N-CARBOXYANHYDRIDE

(75) Inventors: Chong-Ming Chen, Shinchuang; Yu-Liang Liu, Taipei; Ya-Chieh Chao, Taoyuan Hsien; Chien-Huang Wu, Chungho, all of (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 09/853,773

(22) Filed: May 14, 2001

Related U.S. Application Data

(62) Division of application No. 09/689,667, filed on Oct. 13, 2000, now Pat. No. 6,262,274.

(51) Int. Cl.[7] .................................................. C07C 261/00
(52) U.S. Cl. .................................................. 560/24
(58) Field of Search ................................. 560/24

(56) References Cited

U.S. PATENT DOCUMENTS 4,496,541 * 1/1985 Huang et al. ........................ 415/2

* cited by examiner

*Primary Examiner*—Joseph K. McKane
*Assistant Examiner*—Joseph Murray
(74) *Attorney, Agent, or Firm*—Bacon & Thomas

(57) ABSTRACT

A process for preparing N-[1-(S)-ethoxycarbonyl-3-phenylpropyl]-L-alanine N-carboxyanhydride of the following formula (I), (I)

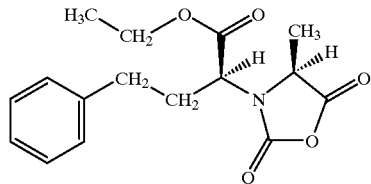

is to react N-[1-(S)-ethyoxy carbonyl-3-phenylpropyl]-L-alanine with XCOOR, wherein X is halogen atom, R is $C_1$–$C_6$ alkyl, to obtain a N-alkoxycarbonyl compound, then reacting with an acyl group activation reagent, finally contact with water. The compound of formula (I) is a key intermediate of ACE inhibitors.

3 Claims, No Drawings

PROCESS FOR PREPARING N-[1-(S)-ETHYOXYCARBONYL-3-PHENYLPROPYL]-L-ANANINE N-CARBOXYANHYDRIDE

This application is a divisional application of U.S. application Ser. No. 09/689,667, filed Oct. 13, 2000, now U.S. Pat. No. 6,262,274 of which the entire disclosure of the pending, prior application is hereby incorporated by reference.

BACKGROUND OF THE INVENTION

1. Field of the Invention

The present invention relates to a process for preparing the prodrug of angiotensin converting enzyme (hereinafter referred to as "ACE") inhibitors. More particularly, it relates to a process for preparing N-[1-(S)-ethyoxycarbonyl-3-phenylpropyl]-L-alanine N-carboxyanhydride (hereinafter referred to as "NEPA-NCA").

2. Description of the Prior Art

Enalapril Maleate of the following, formula (II)

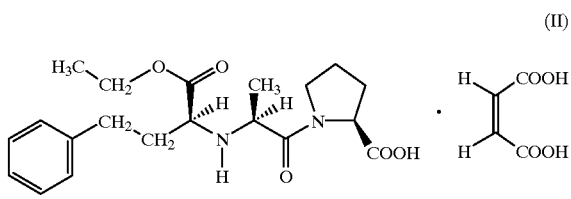

(II)

which is a well-known antihypertensive agent due to an excellent ACE inhibitory activity. EP215335 discloses a process for preparing the formula (II) by using the NEPA-NCA of the formula (I) as starting material which undergo condensation reaction with L-proline under the basic condition to obtain the N-[1-(S)-ethyoxycarbonyl-3-phenylpropyl]-L-alanine (hereinafter referred to as "Enalapril"):

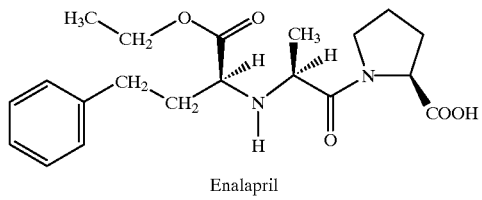

Enalapril

After adding maleic acid, an amino acid salt as the formula (II) can thus be obtained.

Using NEPA-NCA to react with the different amino acids in similar condensation reactions can obtain the different ACE inhibitors, for example, Ramipril, Trandolapril, Delapril, Imidapril and Quinapril-HCl.

The processes for preparing NEPA-NCA of the formula (I) are to react N-[1-(S)-ethyoxy carbonyl-3-phenylpropyl]-L-alanine (hereinafter referred as to "NEPA") of the following formula (III)

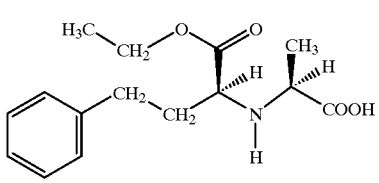

(III)

with phosgene, diphosgene or triphosgene. Those methods are well known and are disclosed in JP57175152A, U.S. Pat. No. 4,496,541 and EP215335. Although the yield of the above phosgene method is relatively high, it is needed to use toxic phosgene in process. As for the purpose of industrial production, there should be a special design for avoiding from the leakage of phosgene, as critical control point for safety control of hazards. Although diphosgene or triphosgene is liquid or solid form at room temperature, however it produces toxic vapor when be heated. Furthermore, the effluents produced by those processes are also pollutive.

U.S. Pat. No. 5,359,086 discloses a non-phosgene method which using N,N'-carbonyldiimidazole instead of phosgene. However N,N'-carbonyldiimidazole is relatively expensive and needs to use phosgene for recovery.

SUMMARY OF THE INVENTION

An object of the present invention is to provide a method to prepare NEPA-NCA without using noxious phosgene, diphosgene or triphosgene.

It is another object of the present invention to provide an economical, safe, simple process of the industrial production of NEPA-NCA.

In accordance with the invention, then, a process is provided for synthesizing NEPA-NCA of the following formula (I),

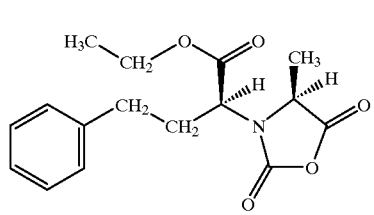

(I)

which comprises reacting NEPA of the following formula (III)

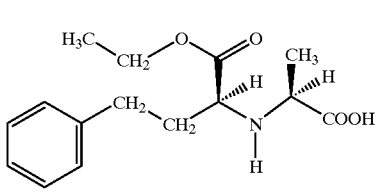

(III)

with XCOOR of the following formula (V),

XCOOR  (V)

wherein X is halogen atom, R is $C_1$–$C_6$ alkyl, to form a N-alkoxycarbonyl compound, then react with an acyl group activation reagent, and finally react with water.

The method of the present invention can use the different amino acids as starting materials to prepare the different N-carboxyanhydride compounds. Examples of the different amino acids are:

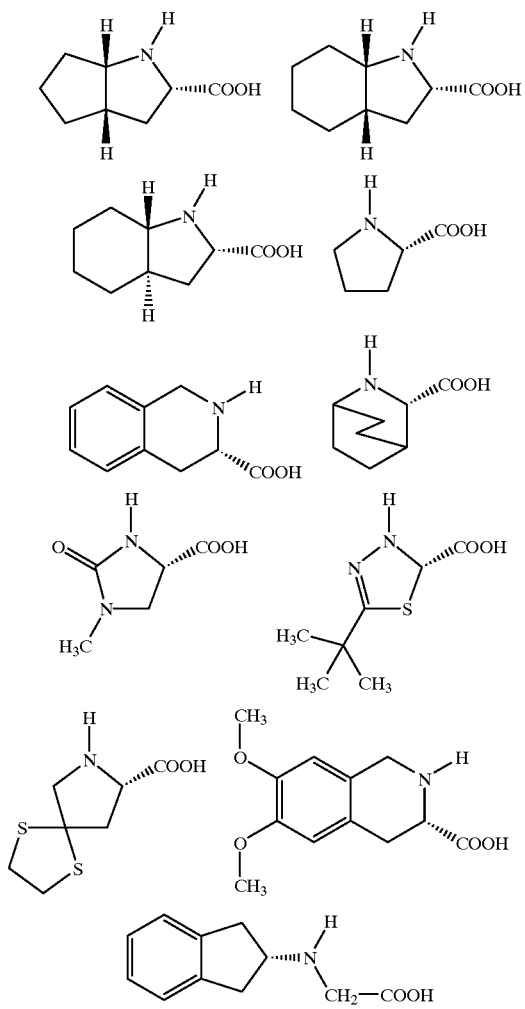

DETAILED DESCRIPTION OF THE PREFERRED EMBODIMENTS

The process of the present invention is shown by the following reaction scheme,

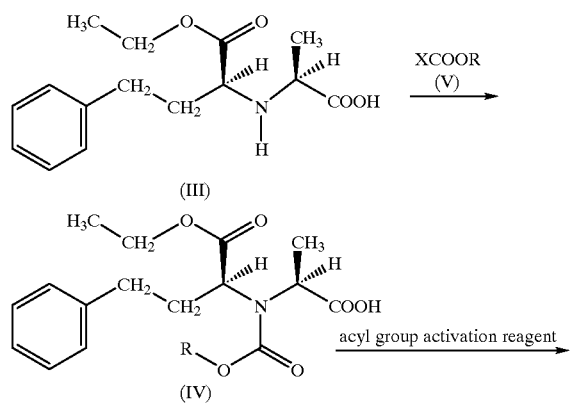

wherein X is halogen atom, R is $C_1$–$C_6$ alkyl.

As shown by the above reaction scheme, NEPA of the formula (III) is reacted with the compound of formula (V) in the presence of organic solvent to form an N-alkoxycarbonyl compound of formula (IV). Then the compound of formula (IV) is reacted with an acyl group activation reagent, and finally contacted with water to obtain the compound of formula (I).

The organic solvents for the reaction can be aprotic solvents, for examples: dichloromethane, dichloroethane, toluene, ethylacetate, hexane, cyclohexane or heptane. It is preferred that said aprotic solvents are dichloromethane, dichloroethane, or toluene, and more preferably is dichloroethane.

It is preferred that the halogen atoms of formula (V) compound are chlorine atom, bromine atom or iodine atom, and more preferably is chlorine atom. Typically, R is, for example, methyl, ethyl, propyl, isopropyl, butyl, isobutyl, tert-butyl, pentyl, isopentyl, or hexyl, and more preferably R is methyl, ethyl, propyl, isopropyl, butyl, isobutyl, or tert-butyl.

The acyl group activation reagent can be acyl chlorination reagent (for example: thionyl chloride or phosphorus pentachloride), acid anhydride or acyl halogen (for example: acetyl chloride), and more preferably is thionyl chloride, acetic anhydride or acetyl chloride.

When NEPA is reacted with formula (V) compound, the reaction temperature is not strictly limited. The range of the reaction temperature can be from 25° C. to 120° C., it depends on what kind of organic solvents used in the reaction. The reaction time is also not strictly limited, and more preferably is 0.45 to 3.0 hours. When N-alkoxycarbonyl compound of formula (IV) is reacted with the acyl group activation reagent, the reaction temperature and the reaction time are depended on what kind of reagents chosen in the reaction. Generally speaking, the reaction temperature is ranged from −10° C. to 120° C. and the reaction time is 2 to 14 hours.

The method of the present invention provides advantages of non-toxic, safety and easy to handle process.

More detailed examples are used to illustrate the present invention, and these examples are used to explain the present invention. The examples below, which are given simply by way of illustration, must not be taken to limit the scope of the invention. In these examples, parts is counted as weight, temperature is Celsius ° C.

EXAMPLE 1

NEPA (27.9 g), dichloroethane (9 ml), ethyl chloroformate (13.1 g) and triethylamine (10 g) were added to a reactor equipped with a mechanical stirrer. The mixture was stirred at room temperature until the reaction was completed. The organic layer was washed with water (2×50 ml) and was adjusted to pH 3–4 by adding HCl. The above organic layer was dried with magnesium sulphate, then filtrated.

Thionyl chloride (13.1 g) was added to a reactor, and the above filtrate was slowly dropped into the reactor at 5~10°

C. The mixture was stirred at room temperature until the reaction was completed. The organic layer was washed with water (2×50 ml), dried with magnesium sulphate, then concentrated to obtain the crude product. The crude product was recrystallized to get a white crystalline of N-[1-(S)-ethoxycarbonyl-3-phenylpropyl]-L-alanine N-carboxyanhydride, yield=70%, mp=68° C.

$^1$H-NMR(CDCl$_3$): δ1.26(t, 3H), δ1.53(d, 3H), δ2.22~2.48 (m, 2H), δ2.66~2.84(m, 2H), δ3.39(q, 1H), δ4.20(d, 2H), δ4.33(d, 1H), and δ7.15~7.34(m, 5H).

EXAMPLE 2

NEPA (27.9 g), dichloroethane (60 ml), ethyl chloroformate (13.1 g) and polyvinylpyridine (9.6 g) were added to a reactor equipped with a mechanical stirrer. The mixture was stirred at room temperature until the reaction was completed. The organic layer was washed with water (2×50 ml) and was adjusted to pH 3–4 by adding HCl. The above organic layer was dried with magnesium sulphate, then filtrated.

Acetyl chloride (10.2 g) was added to a reactor, and the above filtrate was slowly dropped into the reactor at 5~10° C. The mixture was stirred at room temperature until the reaction was completed. The organic layer was washed with water (2×50 ml), dried with magnesium sulphate, then concentrated to obtain the crude product. The crude product was recrystallized to get a white crystalline of N-[1-(S)-ethoxycarbonyl-3-phenylpropyl]-L-alanine N-carboxyanhydride, yield=91%, mp=68° C.

EXAMPLE 3

NEPA (560 g), dichloroethane (1200 ml) and ethyl chloroformate (237.6 g) were added to a reactor equipped with a mechanical stirrer. After stirred for 0.5 hour, 10M NaOH (230 ml) was added to the reactor. The mixture was stirred for 1 hour.

After the reaction was completed, acetyl chloride (188.4 g) was added to the reactor. The mixture was stirred for 2 hours at 85~95° C. Water (800 ml) was added to the reactor and the mixture was stirred at 70~80° C. until the reaction was completed. The organic layer was separated and concentrated to obtain the crude product. The crude product was recrystallized to get a white crystalline of N-[1-(S)-ethoxycarbonyl-3-phenylpropyl]-L-alanine N-carboxyanhydride, yield=82%, mp=68° C.

EXAMPLE 4

NEPA (27.9 g), toluene (60 ml), and ethyl chloroformate (13.1 g) were added to a reactor equipped with a mechanical stirrer. After stirred for 1.0 hour, thionyl chloride (12.6 g) was added to the reactor at room temperature. The mixture was stirred until the reaction was completed. The organic layer was washed with water (2×50 ml), dried with magnesium sulphate, then concentrated to obtain the crude product. The crude product was recrystallized to get a white crystalline of N-[1-(S)-ethoxycarbonyl-3-phenylpropyl]-L-alanine N-carboxyanhydride, yield=53%, mp=68° C.

EXAMPLE 5

NEPA (27.9 g), dichloroethane (90 ml), and ethyl chloroformate (13.1 g) were added to a reactor equipped with mechanical stirrer. After stirred for 1.0 hour, 10M NaOH (10 ml) was added to the reactor. The mixture was stirred for 0.5 hour.

Upon completion of the reaction, acetic anhydride (5.1 g) was added to the mixture. After the salt was removed, thionyl chloride (13.1 g) was added to the reactor. The mixture was stirred at room temperature until the reaction was completed. The organic layer was washed with water (20 ml), dried with magnesium sulphate, then concentrated to obtain the crude product. The crude product was recrystallized to get a white crystalline of N-[1-(S)-ethoxycarbonyl-3-phenylpropyl]-L-alanine N-carboxyanhydride, yield=63%, mp=68° C.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A compound of the following formula (IV):

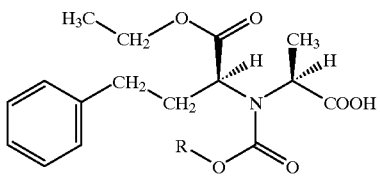

(IV)

wherein R is C$_1$–C$_6$ alkyl.

2. The compound of claim 1, wherein R is methyl, ethyl, propyl, isopropyl, butyl, isobutyl or tert-butyl.

3. The compound of claim 1, wherein R is ethyl.

* * * * *